(12) United States Patent
de Oliveira e Ramos et al.

(10) Patent No.: US 8,041,091 B2
(45) Date of Patent: Oct. 18, 2011

(54) METHODS AND SYSTEMS FOR DETECTION OF RETINAL CHANGES

(75) Inventors: João Diogo de Oliveira e Ramos, Amoreira da Gândara (PT); Nélson Augusto de Sousa Vilhena, Matosinhos (PT); Frederico Teles de Campos Costa Santos, Coimbra (PT); João Paulo da Silva Pinto, Condeixa-a-Nova (PT)

(73) Assignee: Critical Health, SA, Coimbra (PT)

( * ) Notice: Subject to any disclaimer, the term of this patent is extended or adjusted under 35 U.S.C. 154(b) by 0 days.

(21) Appl. No.: 13/046,758

(22) Filed: Mar. 13, 2011

(65) Prior Publication Data

US 2011/0160562 A1 Jun. 30, 2011

Related U.S. Application Data

(63) Continuation of application No. 12/629,798, filed on Dec. 2, 2009.

(51) Int. Cl.
*G06K 9/00* (2006.01)
(52) U.S. Cl. ......... 382/128; 351/206; 715/700; 345/418
(58) Field of Classification Search .................. 382/128; 351/206; 715/700; 345/418
See application file for complete search history.

(56) References Cited

U.S. PATENT DOCUMENTS

| | | | |
|---|---|---|---|
| 6,698,885 B2 | 3/2004 | Berger et al. | |
| 7,177,486 B2 | 2/2007 | Stewart et al. | |
| 7,283,653 B2 | 10/2007 | Zahlmann et al. | |
| 7,474,775 B2 | 1/2009 | Abramoff et al. | |
| 7,488,071 B2* | 2/2009 | Ogawa et al. | 351/206 |
| 7,512,436 B2 | 3/2009 | Petty et al. | |
| 7,520,611 B2 | 4/2009 | Franz et al. | |
| 7,568,800 B2 | 8/2009 | Mihashi et al. | |
| 7,583,827 B2 | 9/2009 | Hansen et al. | |
| 7,593,559 B2 | 9/2009 | Toth et al. | |
| 7,856,135 B1* | 12/2010 | Bernardes | 382/131 |
| 2002/0052551 A1 | 5/2002 | Sinclair et al. | |
| 2004/0105074 A1 | 6/2004 | Soliz et al. | |
| 2005/0171974 A1 | 8/2005 | Doering et al. | |
| 2007/0002275 A1 | 1/2007 | Yan | |
| 2007/0188705 A1 | 8/2007 | Tajima et al. | |

(Continued)

FOREIGN PATENT DOCUMENTS

JP 10-234674 A 9/1998

(Continued)

OTHER PUBLICATIONS

Tsai et al., "Automated Retinal Image Analysis Over the Internet", Jul. 2008, IEEE Transactions on Information Technology in Biomedicine, vol. 12, No. 4, 480-487.*

(Continued)

*Primary Examiner* — Vikkram Bali
*Assistant Examiner* — Katrina Fujita
(74) *Attorney, Agent, or Firm* — SNR Denton US LLP

(57) ABSTRACT

An image analysis system allows users to import digital color fundus images over time, and group such images for processing so as to generate analyses. Analyses are information modules based on a selected group of images and, optionally, related information. An analysis tool allows users to view and manipulate the analyses via a graphical user interface for aid in identifying and classifying microaneurysms and other symptoms related to retinopathy and, more generally, to allow for the detection of retinal changes over time.

17 Claims, 12 Drawing Sheets

U.S. PATENT DOCUMENTS

| | | | |
|---|---|---|---|
| 2007/0214017 A1 | 9/2007 | Profio et al. | |
| 2007/0222946 A1 | 9/2007 | Fukuma et al. | |
| 2007/0258630 A1 | 11/2007 | Tobin et al. | |
| 2008/0059234 A1 | 3/2008 | Hildebrand et al. | |
| 2008/0100612 A1 | 5/2008 | Dastmaichi | |
| 2009/0136100 A1 | 5/2009 | Shinohara | |
| 2009/0143685 A1 | 6/2009 | Elner et al. | |
| 2010/0097574 A1* | 4/2010 | Kushida | 351/206 |
| 2010/0253907 A1* | 10/2010 | Korb et al. | 351/206 |

FOREIGN PATENT DOCUMENTS

| | | |
|---|---|---|
| JP | 2009-022506 A | 2/2011 |
| WO | 0051080 A1 | 8/2000 |
| WO | 0187145 A2 | 11/2001 |
| WO | 03020112 A1 | 3/2003 |
| WO | 2009126112 A1 | 10/2009 |

OTHER PUBLICATIONS

Nappo, A. et al., Unsupervised Change-Detection in Color Fundus Images of the Human Retina, Proceedings of the 7th Nordic Signal Processing Symposium, NORSIG 2006, pp. 134-137, Jun. 7-9, 2006, Rejkjavik, Iceland.

Nayak, Jagadish et al., Automated Identification of Diabetic Retinopathy Stages Using Digital Fundus Images, Journal of Medical Systems, Nov. 13, 2007.

LaLonde, M. et al., RetsoftPlus: a tool for retinal image analysis, Proceedings 17th IEEE Symposium on Computer-Based Medical Systems, CBMS 2004, pp. 542-547. Jun. 24-25, 2004, Montreal, Canada.

Troglio, G et al., Automatic Registration of Retina Images based on Genetic Techniques, 30th Annual International Conference of the IEEE Engineering in Medicine and Biology Society, EMBS 2008, pp. 5419-5424, Aug. 20-25, 2008, Vancouver, Canada.

Quellec, G. et al., Multimedia Medical Case Retrieval Using Decision Tree, 29th Annual International Conference of the IEEE Engineering in Medicine and Biology Society, EMBS 2007, pp. 4536-4539, Aug. 22-26, 2007, Lyon, France.

Tobin, Kenneth W. et al., Using a Patient Image Archive to Diagnose Retinopathy, 30th Annual International Conference of the IEEE Engineering in Medicine and Biology Society, EMBS 2008, pp. 5441-5444, Aug. 20-25, 2008, Vancouver, Canada.

Bernardes, R. et al., Computer-Assisted Microaneurysm Turnover in the Early Stages of Diabetic Retinopathy, Opthalmologicia 2009, vol. 223, No. 5, pp. 284-291, 2009.

Narasimha-Iyer H. et al., Robust detection and classification of longitudinal changes in color retinal fundus images for monitoring diabetic retinopathy, IEEE Transactions on Biomedical Engineering, vol. 53, issue 6, pp. 1084-1098, Jun. 2006.

Cao, Hua et al., Automated registration and fusion of the multimodality retinal images, 40th Southeastern Symposium on System Theory, pp. 371-375, Mar. 16-18, 2008, New Orlean, LA, USA.

Li, Qin et al., Robust Object Extraction and Change Detection in Retinal Images for Diabetic Clinical Studies, 2007 IEEE Symposium on Computational Intelligence in Image and Signal Processing, CIISP 2007, pp. 357-362, Apr. 1-5, 2007, Honolulu, HI, USA.

Asvestas P.A. et al., Registration of Retinal Angiogram Using Self Organizing Maps, 28th Annual Conference of the IEEE Engineering in Medicine and Biology Society, EMBS 2006, pp. 4722-4725, Aug. 30-Sep. 3, 2006, New York, NY, USA.

* cited by examiner

FIG. 6

| Patient name | Age | M/F | Analysis type | Eye | Submitted | Status |
|---|---|---|---|---|---|---|
| Anna Ashley Jordan | 22 | F | Microaneurysm analysis - analysis #023 (5 images) | OD | 24-Mar-2009 | Ready |
| Anna Ashley Jordan | 54 | M | Difference analysis - analysis #027 (6 images) | OD | 14:27 h | Ready |
| Emma Taylor | 35 | F | Microaneurysm analysis; analysis #029 (12 images) | OE | 14:28 h | Ready |
| Frank Thomas Blake | 59 | F | Microaneurysm analysis - analysis #021 (3 images) | OD | 14:28 h | Processing |
| Anna Ashley Jordan | 45 | F | Microaneurysm analysis - analysis #019 (3 images) | OD | 13:40 h | Processing |
| Emma Taylor | 67 | F | Microaneurysm analysis - analysis #017 (6 images) | OE | 09:27 h | Processing |
| Jenny Bernstein | 31 | F | Difference analysis - analysis #031 (6 images) | OE | 13:45 h | Waiting Queue |
| Emma Taylor | 53 | M | Difference analysis - analysis #034 (6 images) | OE | 24-Mar-2009 | Error |
| Anna Ashley Jordan | 47 | M | Microaneurysm analysis - analysis #045 (8 images) | | | |

Patient ID, age and gender 604

Analysis Type & ID 606

Date/Time Submitted 608

Analysis status 610

FIG. 9

Analysis unique ID as title
904

Image set
(images used in the current analysis)
906

Individual images output:
New, Old and
Disappeared Microaneurysms
908

Switch between Outputs and
analysis documentation
914

Computed Turnover rates
910

Graph view
within the analysis timeframe
912

Selected image results and preview.
Double click to further explore.
916

Analysis explorer.
Click to further explore the
current analysis. 902

900

METHODS AND SYSTEMS FOR DETECTION OF RETINAL CHANGES

RELATED APPLICATION

This is a CONTINUATION of and claims priority to U.S. patent application Ser. No. 12/629,798, filed 2 Dec. 2009, incorporated herein by reference.

FIELD OF THE INVENTION

The present invention is directed to systems and methods for the presentation and analysis of digital color fundus images (retinographies) to aid in the diagnosis of retinopathies, e.g., diabetic retinopathy and age-related macular degeneration, among others.

BACKGROUND

Diabetic retinopathy is a cause of blindness in diabetic patients and so it is important to be able to screen patients for evidence of this disease. Such screening typically involves examination of digital color fundus images to identify different symptoms related to the disease: microaneurysms, hemorrhages, vascular abnormalities, among others. In particular, the number, density and locations of microaneurysms are important factors to quantify the progression of diabetic retinopathy in its early stages.

SUMMARY OF THE INVENTION

In order to address the above-described problems, systems and methods for the display and analysis of digital color fundus images to aid in the diagnosis of diabetic retinopathy and other pathologies are provided. In one embodiment, the system includes a record module configured to permit digital color fundus images taken at different times to be imported; an image set module configured to group two or more of said images (e.g., on an eye-by-eye and/or patient-by-patient basis) as part of an analysis; a processing module configured to generate analyses results for selected groups of said images; and an analysis tool set configured to permit viewing of the analysis results, as well as the images, on a eye-by-eye basis and to collect inputs and instructions relating to said analyses and images from a user.

In various instantiations of the invention, the record module allows each image to be associated with various information, including some or all of the following indicators: a date on which the respective image was captured, whether the image is of a right or left eye, the kind of equipment used to capture the image, the field and angle of acquisition, and whether or not mydriasis was used at the time the image was acquired. The image set module is adapted to group selected images either manually (the system automatically disposes them in a chronological manner), or with one image being selected as a reference and images within a designated time interval being grouped with respect to that reference automatically.

The processing module is configured to permit image pre-processing and co-registration and various information analysis. Images may be pre-processed prior to analysis through enhancements in contrast and/or brightness. The analysis of the images is performed so as to automatically detect pathological markers of retinopathy, for example through detection of significant retinal changes over time (e.g., as presented in a sequence of images of a patient), detection, identification and quantification of microaneurysms, and/or detection and identification of other relevant pathological markers of retinopathy. Detecting significant retinal changes over time generally involves automatically detecting changes that manifest between different images, indicating either progression or regression of pathological markers (e.g., microaneurysms) of retinopathy. For example, microaneurysms may be automatically detected and identified in various patient images. In addition, once pathological markers of retinopathy have been detected in the images, the system may suggest a follow-up/referral to an ophthalmologist in accordance with a decision tree or other diagnostic aid.

In addition to presenting the existence of pathological markers of retinopathy, embodiments of the present system are configured to compute clinically relevant information such as microaneurysms formation rates, microaneurysms disappearance rates, and microaneurysms activity levels, for example by means of the number of microaneurysms at each visit, the number of new microaneurysms formed during a follow-up period and the number of microaneurysms that suffered occlusion during the follow-up period. Such computations are made on each analysis and are available for review, along with the images themselves and the analysis results, by the user.

Where instantiated as computer software, the present invention may include an analysis tool that has a log-in module (which may accept user credentials such as a user name and password), a main page, a patient module, a patient dashboard, and an image explorer. The main page permits access to a user dashboard, which tracks analysis jobs either in progress or those that have been already processed but have not yet been reviewed, a patient list, a search page and a new patient registration module. Each patient has a dedicated patient dashboard, which acts as a repository for associated information (e.g., clinical histories and demographic information), images and analyses for the patient and allows a user to explore those images and analyses in detail. The patient information can be displayed in any convenient fashion, for example in a collapsed or expanded view.

The patient dashboard also provides the user an opportunity to choose/view information such as any detected significant retinal changes over time. This may include the detection, identification and quantification of microaneurysms and/or other relevant pathological markers of retinopathy. Through the patient dashboard a user can submit new images to be processed as part of an analysis and can have that analysis information returned in a convenient, timeline view.

The image explorer is configured to permit a user to view the images in detail. Views may be configured to include one, two or multiple images, allowing co-registered side-by-side comparisons of images taken at different times, etc. Full screen and partial screen viewing can be accommodated. Both the image explorer and the analysis explorer have associated tool sets, allowing a user to markup or comment an image or analysis. Such markups or comments are stored as separate layers with the associated image. Tools include zoom features (e.g., magnifying lenses), pointers (which allow selection and repositioning of objects), pencils (which permit drawing), commenting fields for text, lesions identifiers, and measuring tools to indicate distances. A calibration feature allows for accurate scaling, for example with reference to the optic disc and fovea (both of which are automatically detected and may be manually confirmed by the user). Different highlights, colors, display options and screen choices (e.g., backgrounds and the like) can also be used. The comments and/or markups can be viewed, edited and/or deleted according to user wishes.

These and other features of the present invention are discussed in greater detail below.

BRIEF DESCRIPTION OF THE DRAWINGS

The present invention is illustrated by way of example, and not limitation, in the figures of the accompanying drawings, in which:

FIG. 6 illustrates an example of a user dashboard for an instantiation of the present invention when executing on a computer system such as that illustrated in FIG. 1.

FIG. 9 illustrates an example of a microaneurysm analysis output screen for an instantiation of the present invention, in particular for the detection and identification of microaneurysms, when executing on a computer system such as that illustrated in FIG. 1.

DETAILED DESCRIPTION

Figure 1:
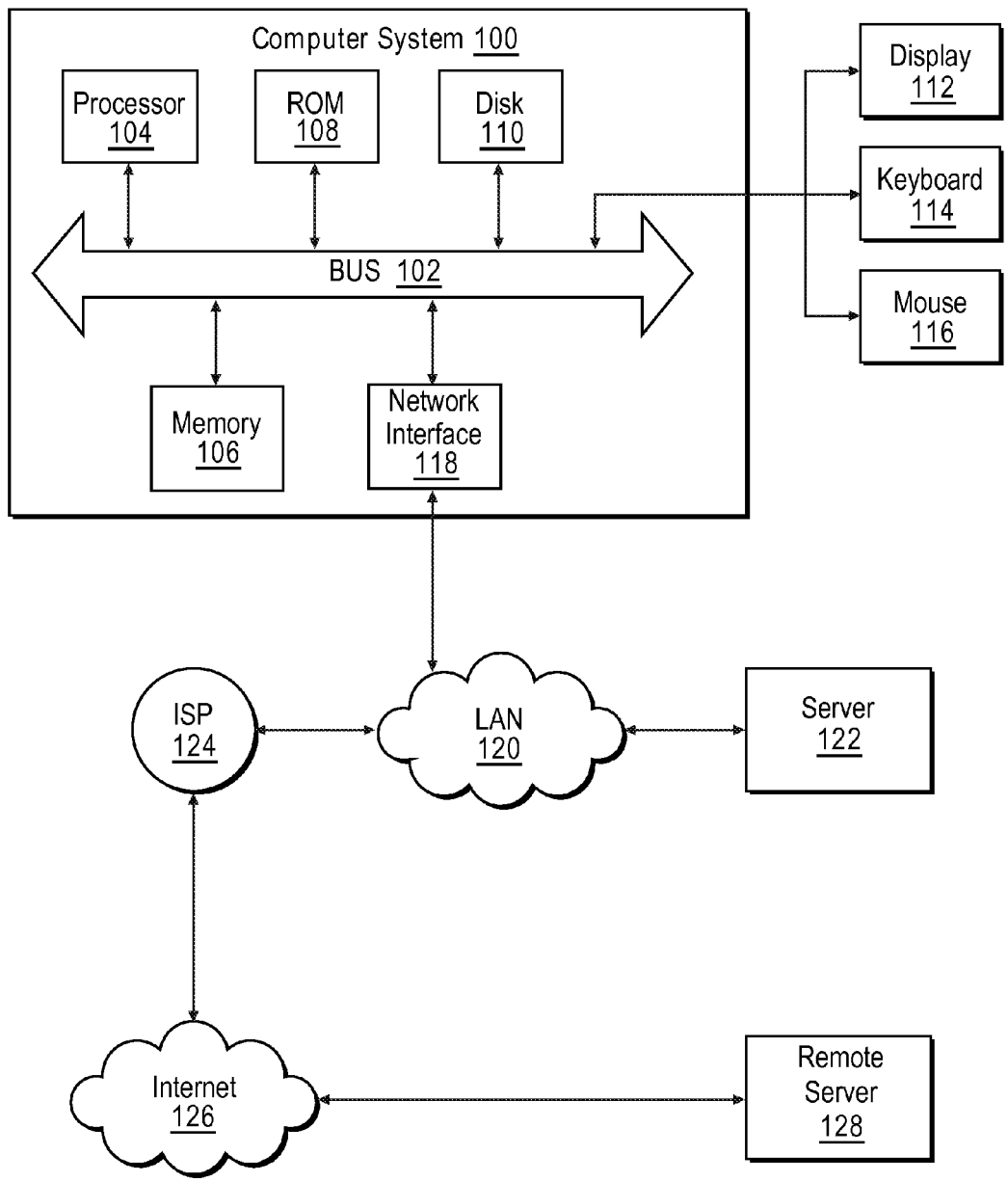
FIG. 1 illustrates an example of a computer system in which embodiments of the present invention may be instantiated.

Described herein are systems and methods for analyzing digital color fundus images. In brief, the present system allows users to import digital color fundus images over time, and group such images for processing so as to generate analyses. Analyses are information modules based on a selected group of images and, optionally, related information. An analysis tool allows users to view and manipulate the analyses via a graphical user interface for aid in identifying and classifying microaneurysms and other features observable in the images, and, more generally, to allow for the detection of retinal changes over time.

In embodiments of the invention, microaneurysms are detected in identified locations, allowing the system to compute microaneurysm turnover indicators such as formation and disappearance rates. Additionally the present system automatically highlights differences between retinographies and clearly identifies changes difficult to be detected by the human eye. The system includes an analysis explorer that includes a tool set, allowing a user to document, draw-over and comment images, as well as an on-screen dashboard. A variety of reports can be created and images archived.

Various embodiments of the present invention may be implemented with the aid of computer-implemented processes or methods (i.e., computer programs or routines) that may be rendered in any computer language including, without limitation, C#, C/C++, Matlab, assembly language, markup languages, and the like, as well as object-oriented environments such as the Common Object Request Broker Architecture (CORBA), Java™ and the like. In general, however, all of the aforementioned terms as used herein are meant to encompass any series of logical steps performed in a sequence to accomplish a given purpose.

In view of the above, it should be appreciated that some portions of the detailed description that follows are presented in terms of algorithms and symbolic representations of operations on data within a computer system memory or other data store. These algorithmic descriptions and representations are the means used by those skilled in the computer science arts to most effectively convey the substance of their work to others skilled in the art. An algorithm is here, and generally, conceived to be a self-consistent sequence of steps leading to a desired result. The steps are those requiring manipulations of representations physical items, such as performing enhancements or other operations involving fundus images of the eye. Usually, though not necessarily, these quantities take the form of electrical or magnetic signals capable of being stored, transferred, combined, compared and otherwise manipulated. It has proven convenient at times, principally for reasons of common usage, to refer to these signals as bits, values, elements, symbols, characters, terms, numbers or the like. It should be borne in mind, however, that all of these and similar terms are to be associated with the appropriate physical quantities and are merely convenient labels applied to these quantities. Unless specifically stated otherwise, it will be appreciated that throughout the description of the present invention, use of terms such as "processing", "computing", "calculating", "determining", "displaying" or the like, refer to the action and processes of a computer system or systems, or similar electronic computing device, that manipulates and transforms data represented as physical (electronic) quantities within its registers and memories into other data similarly represented as physical quantities within its memories or registers or other such information storage, transmission or display devices.

The present invention can be implemented with an apparatus to perform the operations described herein. This apparatus may be specially constructed for the required purposes, or it may comprise a computer system that has been selectively activated or configured by a computer program executed by the computer system. Such a computer program may be stored in/on a computer-readable storage medium, such as, but not limited to, any type of disk including floppy disks, optical disks, CD-ROMs, and magnetic-optical disks, read-only memories (ROMs), random access memories (RAMs), electrically programmable ROMs (EPROMs), electrically erasable and programmable ROMs (EEPROMs), magnetic or optical cards, or any type of tangible media suitable for storing electronic instructions, and each readable by a computer system processor or the like.

The algorithms and processes presented herein are not inherently related to any particular computer or other apparatus. Various general-purpose systems (which become special purpose systems once appropriately programmed) may be used with programs in accordance with the teachings herein, or it may prove convenient to construct more specialized apparatus to perform the required methods. For example, any of the methods according to the present invention can be implemented in hard-wired circuitry, by programming a general-purpose processor or by any combination of hardware and software. One of ordinary skill in the art will immediately appreciate that the invention can be practiced with computer system configurations other than those described below, including hand-held/mobile devices, multiprocessor systems, microprocessor-based and/or digital signal processor-based devices, and the like. The invention can also be practiced in distributed computing environments where tasks are performed by remote processing devices that are linked through a communications network. The required structure for a variety of these systems will appear from the description below.

Referring now to FIG. 1, an exemplary computer system 100 upon which an embodiment of the invention may be implemented is shown. Computer system 100 includes a bus 102 or other communication mechanism for communicating information, and a processor 104 coupled with the bus 102 for executing the computer software which is an embodiment of the invention and for processing information (such as digital color fundus images) in accordance therewith. Computer system 100 also includes a main memory 106, such as a RAM or other dynamic storage device, coupled to the bus 102 for storing information and instructions to be executed by processor 104. Main memory 106 also may be used for storing temporary variables or other intermediate information during execution of instructions to be executed by processor 104. Computer system 100 further includes a ROM or other static storage device 108 coupled to the bus 102 for storing static information and instructions for the processor 104. A storage device 110, such as a hard drive or solid state storage device, is provided and coupled to the bus 102 for storing information and instructions.

Computer system 100 may be coupled via the bus 102 to a display 112, such as a liquid crystal display (LCD) or other display device, for displaying information to a user. An input device 114, including alphanumeric and other keys, is coupled to the bus 102 for communicating information and command selections to the processor 104. Another type of user input device is cursor control 116, such as a mouse, a trackball, or cursor direction keys for communicating direction information and command selections to processor 104 and for controlling cursor movement on the display 112. This input device typically has two degrees of freedom in two axes, a first axis (e.g., x) and a second axis (e.g., y) allowing the device to specify positions in a plane.

In embodiments of the invention which are instantiated as computer programs (i.e., computer-readable/executable instructions stored on a computer-readable medium), such programs are typically stored on storage device 110 and at run time are loaded into memory 106. Processor 104 then executes sequences of the instructions contained in main memory 106 to perform the steps described below. (In alternative embodiments, dedicated circuitry or modules (or, in some cases, firmware-enabled application specific integrated circuits or specialized processors) may be used in place of or in combination with computer software instructions to implement the invention.

Computer system 100 also includes a communication interface 118 coupled to the bus 102. Communication interface 108 provides a two-way data communications between computer system 100 and other devices, for example via a local area network (LAN) 120. These communications may take place over wired and/or wireless communication links. In any such implementation, communication interface 118 sends and receives electrical, electromagnetic or optical signals which carry digital data streams representing various types of information. For example, two or more computer systems 100 may be networked together in a conventional manner with each using the communication interface 118.

Network 120 may also provides communication to one or more networks and other devices associated with those networks. For example, network 120 may provide a connection to a server 122 (which may store images for processing) and/or to data equipment operated by an Internet Service Provider (ISP) 124. ISP 124 in turn provides data communication services through the world wide communication network now commonly referred to as the "Internet" 126, through which remote computer systems such as remote server 128 may be accessed.

Figure 2:
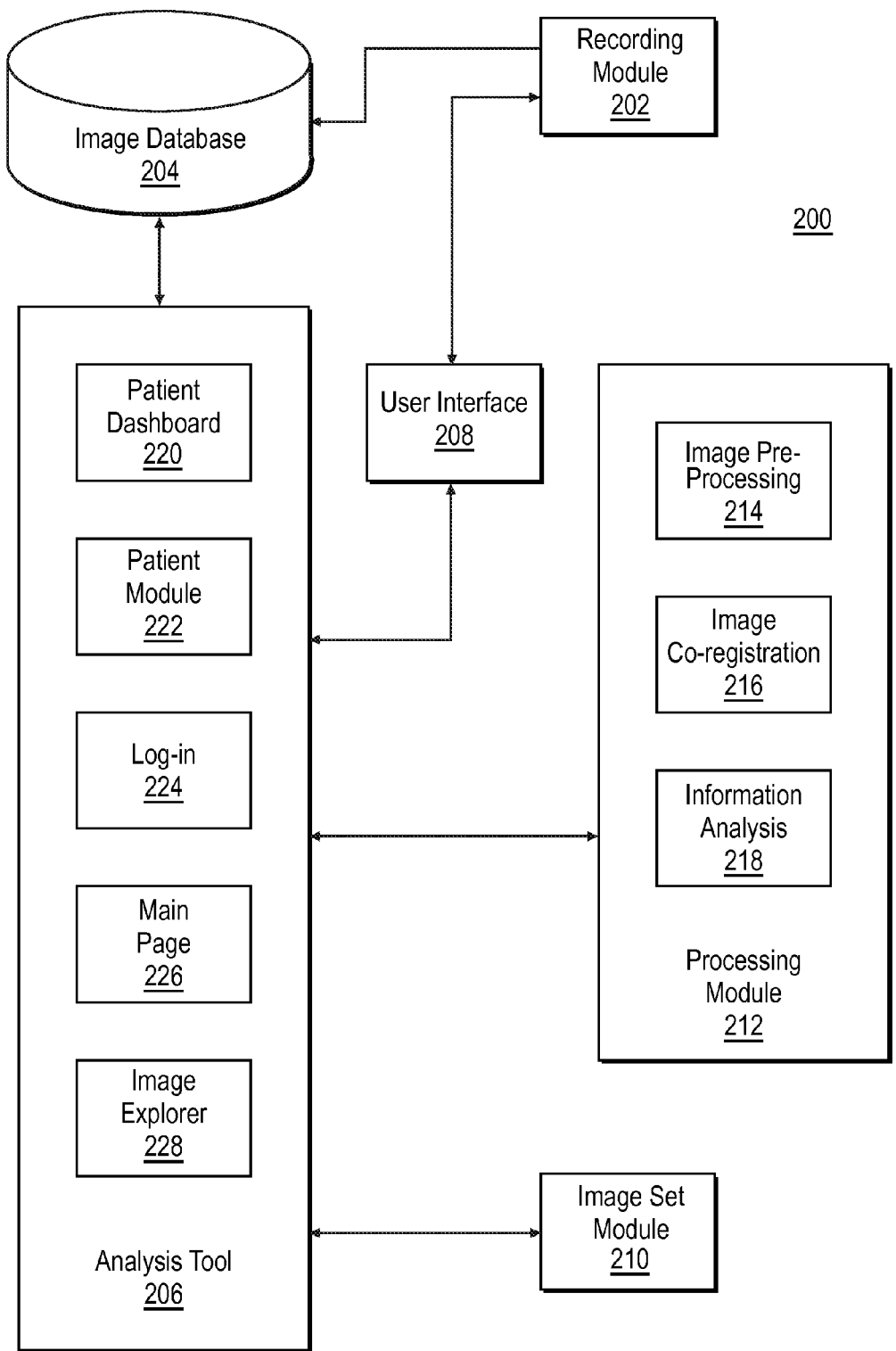
FIG. 2 illustrates an example of an image processing system configured according to an embodiment of the present invention.

Referring to FIG. 2, an example of an image processing system 200 configured according to an embodiment of the present invention is illustrated. System 200 includes a recording module 202 configured to allow digital color fundus images to be added to an image database 204 over time. In one embodiment, the database 204 is located locally, at a personal computer on which an instantiation of system 200 is executing, or may be located remotely for example at a network server 122 or a remote server 128.

System 200 also includes an analysis tool 206 which manages the input and output of information from/to a user interface 208. In practice, the user interface 208 may be presented via a display, such as display 112, and may be adapted to receive alphanumeric and/or cursor control inputs via a keyboard 114 and/or a cursor control device 116. The user interface is adapted, as discussed in detail below, to display information to a user and collect inputs and instructions from a user, said instructions generally relating to the manipulation and control of images to allow for noninvasive diagnosis for retinopathies.

Associated with analysis tool 206, more specifically with its patient dashboard module 220, is an image set module 210, which is configured to permit grouping of digital color fundus images as part of the analysis thereof. The actual analysis is performed by a processing module 212, configured to generate information to aid in diagnostic activities based on a selected group of the images.

As mentioned above, recording module 202 allows for digital color fundus images to be imported and stored in database 204. Along with the images themselves, various information may be imported and stored with the images. For example, information such as the date the image was captured, an indication of whether the image is of a right or left eye, the kind of equipment used to capture the image, and the field and angle of acquisition, and whether or not mydrasis was used at the time the image was captured, can all be recorded and associated with each image as part of database 204. Such information is recorded at the same time as the image is imported.

As will be explained in greater detail below, analysis of the digital color fundus images requires images to be selected, selected images thus comprising an analysis set images, in order to observe differences between images of the same eye that were captured at different times. Accordingly, image set module 210 is adapted to group images either manually (through user direction via interface 208), or automatically. In one embodiment, images are grouped, patient-by-patient, in a chronological order with one image being selected as a reference, a time interval defined, and all images with a date indicator falling within that interval being grouped automatically.

Once selected to define the analysis set, the images can be processed by processing module 212. The processing module includes sub-modules for image pre-processing 214, image co-registration 216 and information analysis 218. Examples of image pre-processing and co-registration are provided in co-pending application Ser. No. 12/629,661, filed on even date herewith. In general, the image pre-processing sub-module 214 is adapted to enhance digital color fundus images by applying changes in contrast and brightness. Co-registration sub-module 216 is adapted to co-register the pre-processed images so that the features in the images are aligned with one another across different images.

The information analysis sub-module 218 is adapted to detect pathological markers of retinopathy by detecting significant retinal changes over time; detecting, identifying and quantifying microaneurysms that appear in the images; and/or detecting and identifying other relevant pathological markers of retinopathy. For each individual patient, detecting significant retinal changes over time involves automatically detecting differences that exist between different images of a common eye, indicating either progression or regression of pathological markers of retinopathy. Detecting and identifying microaneurysms involves automatically detecting and identifying microaneurysms in the various images.

The information analysis sub-module 218 is further adapted to permit exploration of the information obtained from the analysis of the digital color fundus images by computing the position and areas of detected pathological signs of retinopathy and, in some instances, suggest recommended referral/follow-up actions in accordance with a decision tree. Computation of the position and areas of detected pathological signs of the retinopathy involves computation of the position and surface area of, for example, microaneurysms detected in the images. Clinically relevant information that can be obtained in this fashion includes microaneurysm formation rate; microaneurysm disappearance rate; and microaneurysm activity level (for example by determining the number of microaneurysms at each visit/image capture, the number of new microaneurysms during a prescribed follow-up period and the number of microaneurysms that suffered occlusion during the follow-up period).

As shown in the illustration, analysis tool 206 receives as inputs images added to database 204 by the user and returns information gleaned from those images as determined by processing module 212. The analysis tool includes a variety of sub-modules, such as a log-in or registration module 224, a main page 226, a patient module 222, a patient dashboard 220, and an image explorer 228. The log-in/registration module 224 is configured to restrict access to system 200 by authorized users, e.g., those that have a valid user name/password combination, which can be entered via the user interface 208.

Upon a successful log-in, the main page 226 is displayed via the user interface and provides a variety of options, including a jobs dashboard, which includes a list of submitted jobs (i.e., analysis projects) that are in progress, waiting in queue, have failed or have finished successfully but are as-yet un-reviewed; a patient tab; a search tab, which allows the user to search for a particular patient, rather than selecting the one from a default list displayed in the patient tab; and a "new" tab, to add new patients to the system. The various sub-modules or tabs, when selected, may launch new windows in the user interface which facilitate user interaction with the features provided by those sub-modules. The new tab provides facilities for the user to create new patient records, which can contain associated images and information and any analyses of those images.

Patient module 222 is the collection of patient files, accessed by means of selection though the patient or search tab in the main page. Within the patient module, information and analyses pertaining to a respective individual patient is displayed via user interface 208 for user review and interaction. Patient information may include general identification information and a brief clinical history of the respective patient. An expanded/collapsed viewing scheme allows the user to review only that information which is of interest at the time. Within the patient module 222, the user may create, edit and delete aspects of a respective patient's records, and can also launch the patient dashboard 220, populated with images and information related to the selected patient.

Patient dashboard 220 comprises a display of images, analysis results and in-progress analyses related to the selected patient. The dashboard is configured to provide the user the opportunity to choose various information analyses, on a right eye/left eye basis, such as the detection of significant retinal changes over time; the detection, identification and quantification of microaneurysms; and the detection and identification of other relevant pathological markers of retinopathy. Further, via the dashboard a user can submit new images (right eye and/or left eye) to be processed.

Image explorer 228 provides a separate window in user interface 208 in which a user may view a full-screen version of digital color fundus images. The images may be displayed individually, or two at a time or even four at a time in a common screen. This multi image display capability allows a user to review how images of the same eye, taken at different times, compare with one another and thereby aids in the doctor's diagnostic process. Images can be selected for display in time sequence or in another order selected by the user. Such selection may be made by dragging and dropping representations of the images into the image explorer. Images can be seen in the image explorer if opened directly from the image database (in which case only one image is visible) or opened through an analysis (in which case the images of that analysis may be compared).

The image explorer also includes a variety of image review tools, such as a zoom capability (e.g., using a magnifying glass object that can be dragged over portions of the image, various drawing and marking tools (e.g., pointers which allow for selection and repositioning of objects, pencils which allow for free drawing by a user, text and commenting tools, rulers or other measuring devices, lesion identifiers, and calibration instruments which correspond to a user's validation of automated detection of features such as the optic disc and fovea within a respective image), various overlay tools, allowing different background images to be overlaid with analysis results, comments, drawings, matrices showing principle components or axes of the eye, and colors used to highlight items of significance, such as lesions and the like.

Having thus provided an overview of system 200, a detailed discussion of the operation of the various modules thereof will now be presented. This will be done from the point of view of a user of system 200, and will include a presentation of various screens of user interlace 208. This user-oriented discussion is intended to provide an example of the user of system 200, but the system need not be used in the order presented. The discussion assumes that a software instantiation of system 200 has been installed on a compatible computer system, such as computer system 100 shown in FIG. 1, and that the software is running on that system. This may require, the installation of a conventional operating system, such as the Windows™ operating system available from Microsoft Corporation of Redmond, Wash., or another operating system, and other conventional components of a computer system, such as a browser, etc.

Figure 3:
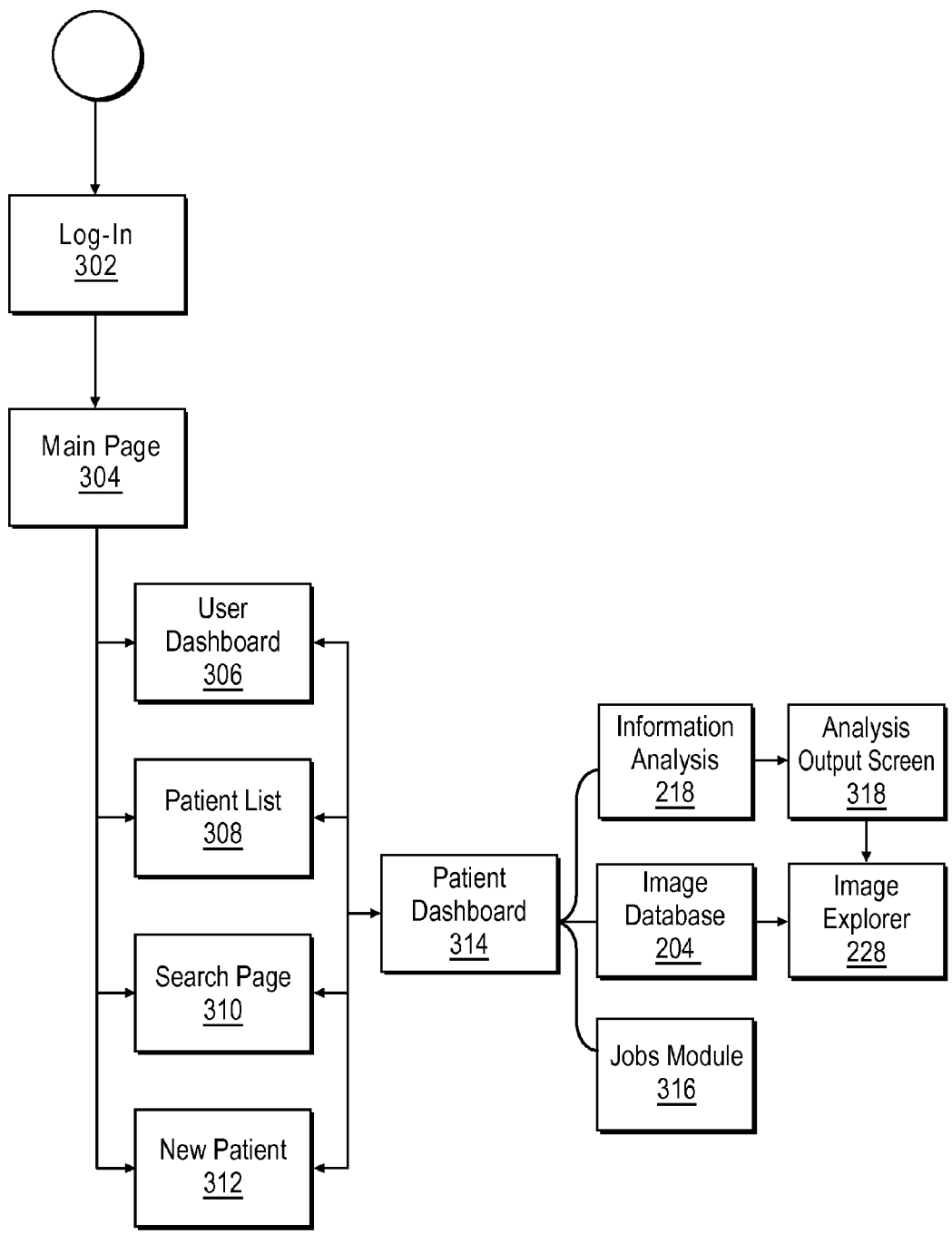
FIG. 3 illustrates an example of a program flow for a user of an instantiation of the present invention, when executing on a computer system such as that illustrated in FIG. 1.
Figure 4:
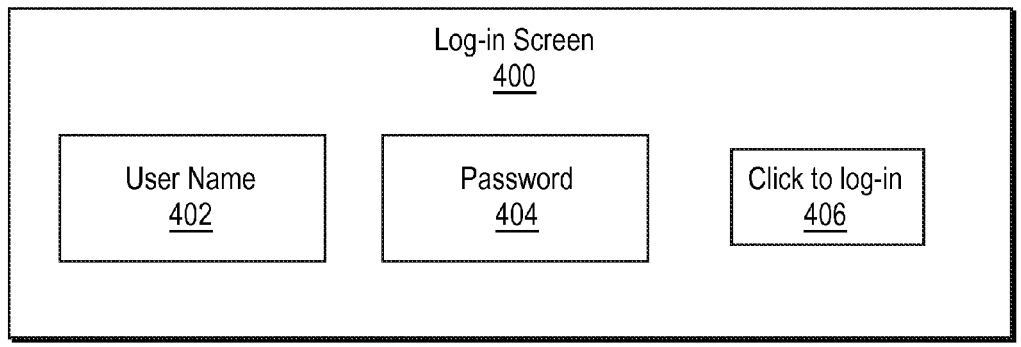
FIG. 4 illustrates an example of a log-in screen for an instantiation of the present invention when executing on a computer system such as that illustrated in FIG. 1.

Referring to FIG. 3, use of system 200 begins with a user logging-in 302 by entering his or her user credentials. Typically, this will be a user name/password combination, but other credentials can be used. For example, in some instances a user may be required to provide a cryptographic key or other means of identification. An example of a log-in screen 400 is shown in FIG. 4. Log-in screen 400 includes text boxes 402 and 404 that permit a user to enter a user name and password, respectively, and a button 406. Upon selection of button 406, e.g., using cursor control device 116 or keyboard 114, the log-in process takes place. Of course, in some cases, system 200 may be configured to run without requiring the user to successfully navigate any identification challenge. Where such identification is required, however, a log-out facility may also be provided so that users can secure system 200 when it is not in use. In some cases, the user may be automatically logged-out after a defined period of inactivity in which system 200 does not receive any user input.

Figure 5:
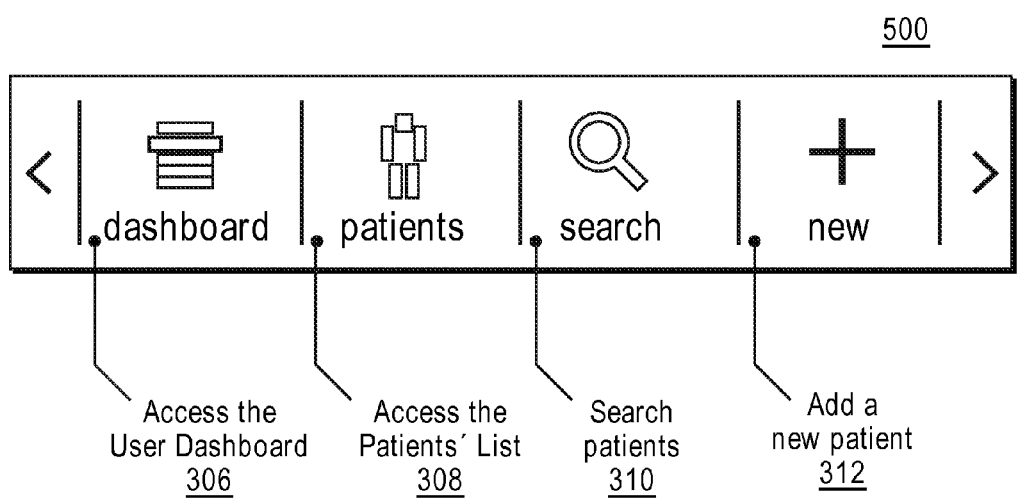
FIG. 5 illustrates an example of a main page for an instantiation of the present invention when executing on a computer system such as that illustrated in FIG. 1.

Upon successful log-in, the main page module 304 is displayed for the user, preferably in the form of a menu. An example of a main page menu 500 is shown in FIG. 5. In some instances, this menu is displayed, either fully or in a minimized fashion, in a reserved area of the screen or as an overlay over a currently displayed window. This allows the user to always have the option of navigating between the components accessed through the main page, i.e., the user dashboard 306, patient list 308, search page 310 and new patient page 312.

The user dashboard 306 displays those analyses which a user has submitted but which have not yet been reviewed. FIG. 6 presents an example of a user dashboard screen 600. Within screen 600, an analysis status menu 602 is presented. This menu includes, for each analysis, a patient identification (ID) 604, including age and gender, an analysis IP (including analysis type) 606, and the date and time 608 when the analysis was submitted. Analyses generally require some time to be processed and so it is expected that users will queue up several analyses (image comparison jobs) to be processed in the background which other tasks (such as the review of individual images or of previously submitted analyses) are performed in the foreground. System 200 will alert the user, via an appropriately displayed analysis status message 610 in the user dashboard, when an analysis is ready for review. Such review can be undertaken by selecting the completed analysis from the user dashboard. Upon review, an analysis is removed from the user dashboard but it is available in the respective patient dashboard for the patient to which it pertains. In addition to showing analyses that are ready for review, the user dashboard also lists analyses which are still being processed, those which are awaiting processing, and those which may have stopped processing prematurely due to errors in co-registration or otherwise.

Figure 7:
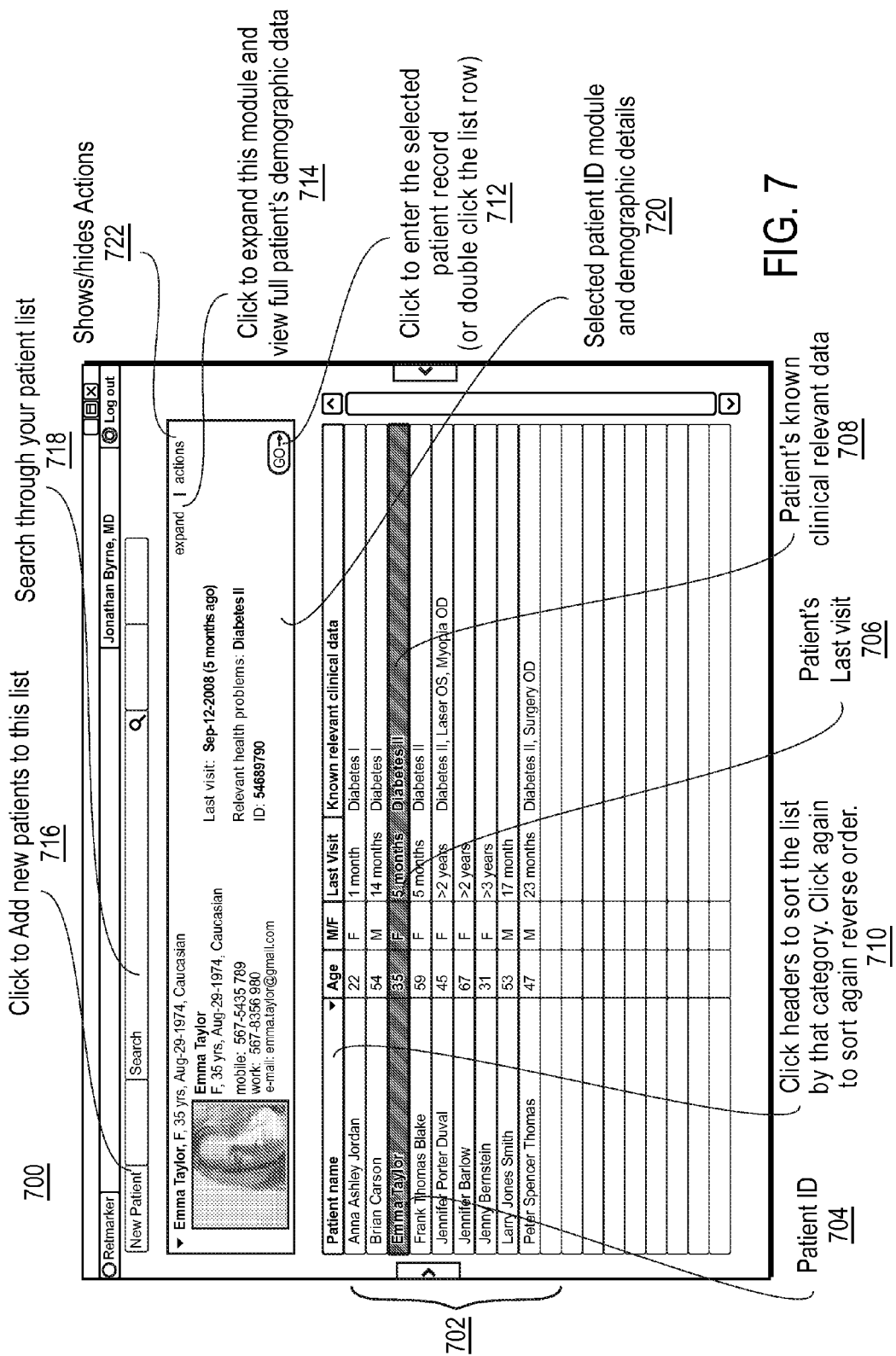
FIG. 7 illustrates an example of a patient record selected from a patient list for an instantiation of the present invention when executing on a computer system such as that illustrated in FIG. 1.

The patients list 308 allows access to individual patient images and information in the form of a patient's record. An example of a patient list screen 700 is shown in FIG. 7. Within the screen, an alphabetical list 702 of the user's patients is presented by default. Each record includes the patient ID 704, the date of the patient's last visit 706, and any known, relevant clinical information 708. The list can be sorted in a variety of ways 710 to suit the user's requirements.

When an individual patient record is selected from list 702, it is shown in detail 720 within the screen and any associated actions can be revealed or hidden 722. From the patient list a user can access a respective patient record 712, edit the patient's demographic data 714, add or remove patients from a list 716 and also filter the patient list using a search feature 718. Alternatively, the user may use the search page 310 to search for a particular patient. New patient records can be added using the new patient module 312. Selecting a patient record in any of these fashions opens the respective patient dashboard 314.

Figure 8:
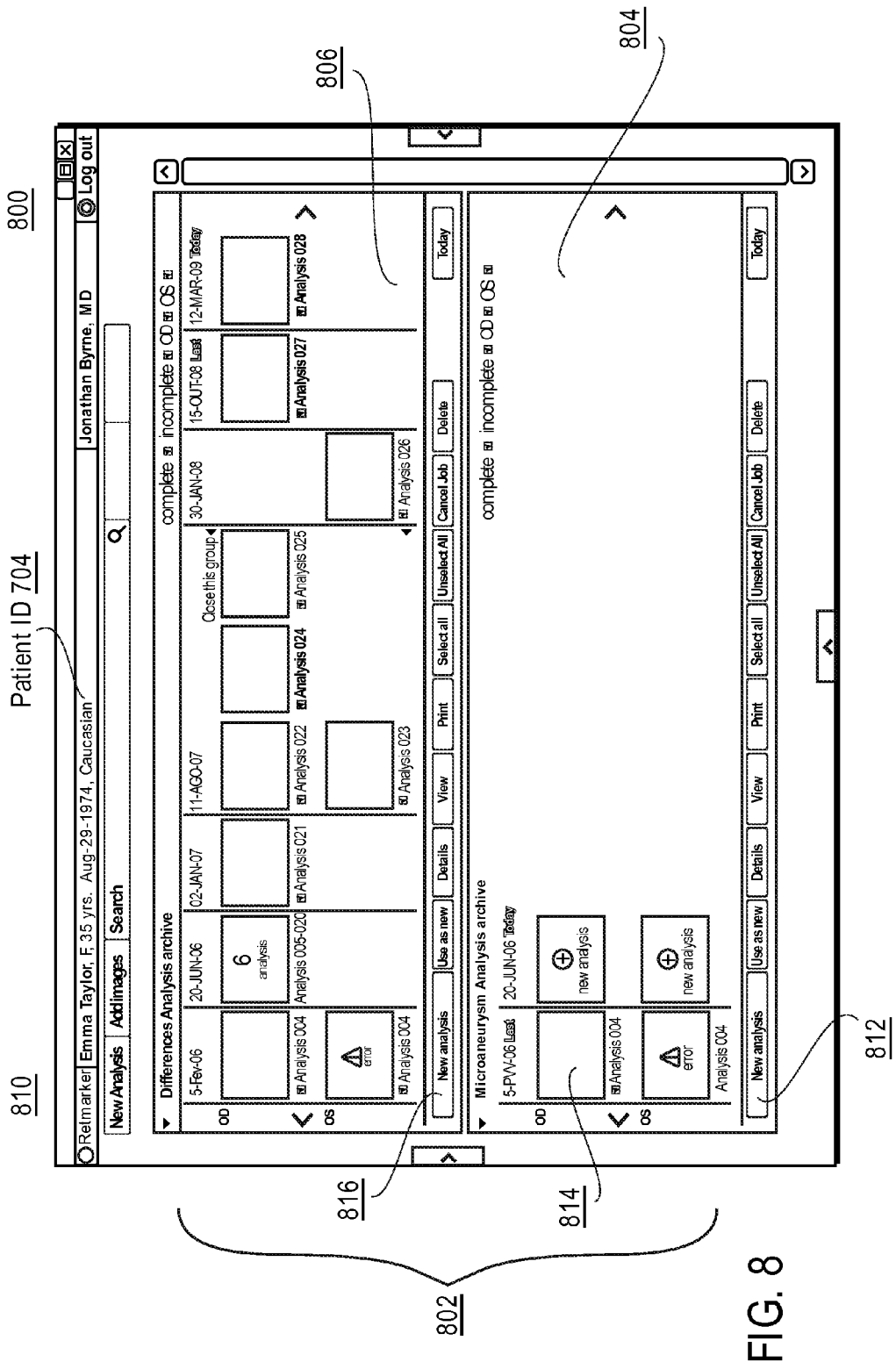
FIG. 8 illustrates an example of a patient dashboard for an instantiation of the present invention when executing on a computer system such as that illustrated in FIG. 1.

An example of a patient dashboard 800 is shown in FIG. 8. The patient dashboard displays an overview of the analyses 802 (corresponding to the information module) for the selected patient. This information is laid out in timeline-style modules for both right and left eyes: images and analyses from both eyes are displayed one above the other, for example organized by date of image capture. Users can navigate between the data displayed in these modules using cursor control keys on a keyboard or a cursor control device. By way of example, a patient dashboard may display a scrollable timeline 804 containing OD (right eye) and OS (left eye) microaneurysm analyses, a scrollable timeline 806 containing OD and OS differences analyses, an OD and OS image database (not shown in this illustration but selectable at the user's option) displaying previously imported OD and OS images, and a jobs module (not shown in this illustration) displaying analyses submitted but not yet ready for the selected patient.

Each patient dashboard thus provides an image database for the associated patient, i.e., an archive of the respective patient's available images, organized in a scrollable timeline containing images from OD and OS. To import images into a patient dashboard, a user needs only to access that dashboard, e.g., from the patient list, and select an "add image" button 810. This will provide the user an appropriate screen where the user will be prompted for images he/she wishes to import from database 204 or from external sources. Images may be selected for import in any of a variety of fashions, for example by selecting associated checkboxes or by dragging the images into an appropriate portion of the screen. At the time an image is imported, a user may be prompted to provide additional details such as the date of the image (i.e., the date it was captured), the field of view, whether it is an OS or OD image, the angle, etc.

From the patient dashboard, the user can also create new analyses for a patient. Two different types of analyses can be done: microaneurysm analyses and differences analyses. As the name implies, a microaneurysm analysis examines image sets for microaneurysms that appear within the constituent images. Microaneurysm determinations can be made by comparing features found in an image under consideration with a reference pattern. While the microaneurysm analysis is run on an image-by-image basis, results are reported with respect to image sets so that microaneurysm turnover rates can be computed and reported. Microaneurysm detection is an automated process. Differences analyses examine sets of images against a designated baseline or reference image to determine differences between the baseline and another image. Differences detections can reveal features such as hemorrhages, drusen, exudates, etc. Differences detections result in differences being highlighted, but no automated characterization of the difference is provided. Instead, it is left to the user to examine the highlighted difference and decide what it represents.

For a microaneurysm analysis for a patient, it is preferable to use at least three representative images taken over a minimum twelve month period. From the patient dashboard, the user selects a "new analysis" button 812, and in response a user interface screen which permits the user to select the images to be used in the analysis will be presented. The user can select any number of images, preferably three or more (per eye), for the analysis, and both OS and OD analyses can be run simultaneously. When the desired images for analysis have been selected, the user can instruct the analysis module to begin processing the new analysis.

When an analysis is complete, the results are returned to the patient dashboard for review in the form of a microaneurysm analysis output. The analysis output includes the image set used for the analysis, the microaneurysm count for each such image and the computed microaneurysm turnover rates (microaneurysm formation and disappearance rates). In other instances, the analysis will compare each selected image to a baseline image and highlight relevant differences. To review a microaneurysm analysis the user selects the appropriate patient (e.g., from the patients list) and enters his/her associated patient dashboard. The available analyses will be presented in the scrollable timeline 806 containing OS and OD microaneurysm analyses and can be opened by appropriate selection (e.g., a double click on an analysis thumbnail 814). Once opened, the selected analysis will be presented for review in an analysis output screen 318, which may be presented in a separate window.

In the case of a differences analysis, the process is similar. From the patient dashboard, the user selects a new differences analysis button 816 and identifies the image dataset which the user wishes to analyze. When the differences analysis is complete, the results are returned to the patient dashboard for review in the form of a differences analysis output. Selecting the differences analysis will then allow the user to review the results in a differences analysis output screen, which may be presented in a separate window. This is discussed in greater detail below, with reference to FIG. 13.

Within a microaneurysm analysis output screen 900, an example of which is shown in FIG. 9, an analysis explorer 902 is provided. The analysis explorer contains a toolset to allow the user to document (e.g., using pencil and pointer tools), zoom in (using a magnifying lens tool), comment (using a text tool), measure (using a ruler tool) and compare all features in each individual image included in an analysis. These images can also be compared side-by-side, enhancing the user's ability to identify clinically significant features in the images and visually inspect the progression of those features in succeeding images. In some instantiations, individual images from the image database, which are not part of any analysis, can also be explored, and, optionally, commented, using the analysis explorer (e.g., for comparison purposes). Special tools allow the user to designate or mark (e.g., with appropriate icons) features as microaneurysms, hemorrhages, exudates, vascular caliber abnormalities, or drusens. In addition, a calibration tool allows for fine tuning of the auto-detection of the optic disc and fovea in each image. As analyses are added to a patient's dashboard they are saved, allowing the user to return to previous analyses to compare results from various analyses over time. Analyses not yet ready for review can be monitored in the jobs module, which displays progress of queued jobs.

Regarding a microaneurysms analysis output, the system allows the user to interact with the automatically identified microaneurysms. The user may reclassify microaneurysms as being already existent or inexistent. The user may also add microaneurysms using a tool designed for that effect. When a microaneurysm is manually marked, it is propagated, as an empty placeholder, through all the other images of the analysis. The system also offers to the user a tool (a set of navigation arrows that appear near the marked microaneurysm/placeholder) for fast, centered, browsing through the referred placeholders, allowing the user to classify them as being visible or not visible.

Each microaneurysm analysis is provided a unique ID 904 to permit its identification. Within the output screen, the individual images 906 that make up the set of images used to computer the analysis are provided. As shown, these images are arranged in a timeline fashion, allowing the user to observe changes over time. In addition, to the actual images, the computed differences 908 between the images are displayed. These differences highlight microaneurysms which were located in the images. In addition, factors such as microaneurysm turnover rates (determined from comparisons of the number of microaneurysms found in different images taken over time) are presented both numerically and graphically, 910 and 912, and users can switch between outputs and analysis documentation 914, displayed on the right side of the screen. Individual images can also be explored further by activating the image explorer 916.

Figure 10:
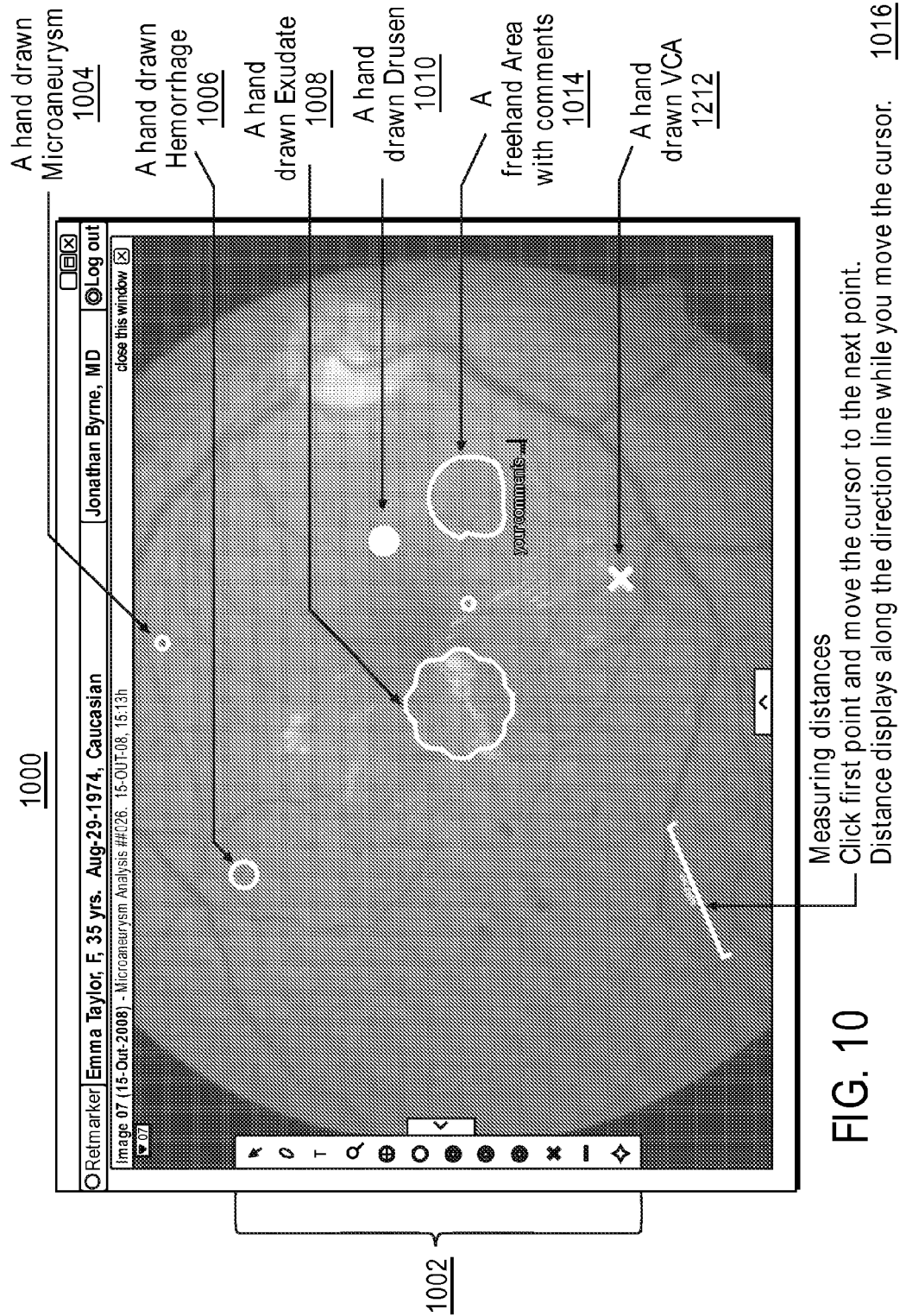
FIG. 10 illustrates an example of an analysis explorer screen for an instantiation of the present invention when executing on a computer system such as that illustrated in FIG. 1.

An example of the analysis explorer screen 1000 is shown in FIG. 10. Illustrated alongside the image under consideration are icons representing the toolset 1002 discussed above and examples of the commenting and other outputs that can be produced using these tools is shown. For example, in this screen, a user has indicated one microaneurysm 1004, hemorrhages 1006, exudates 1008, drusen 1010, and VCAs 1012. The user has also annotated the image with comments 1014. An example of measuring tool 1016 is also shown. Users can manipulate the measuring tool by dragging and dropping the ends of the ruler onto locations of interest in the image.

Figure 11:
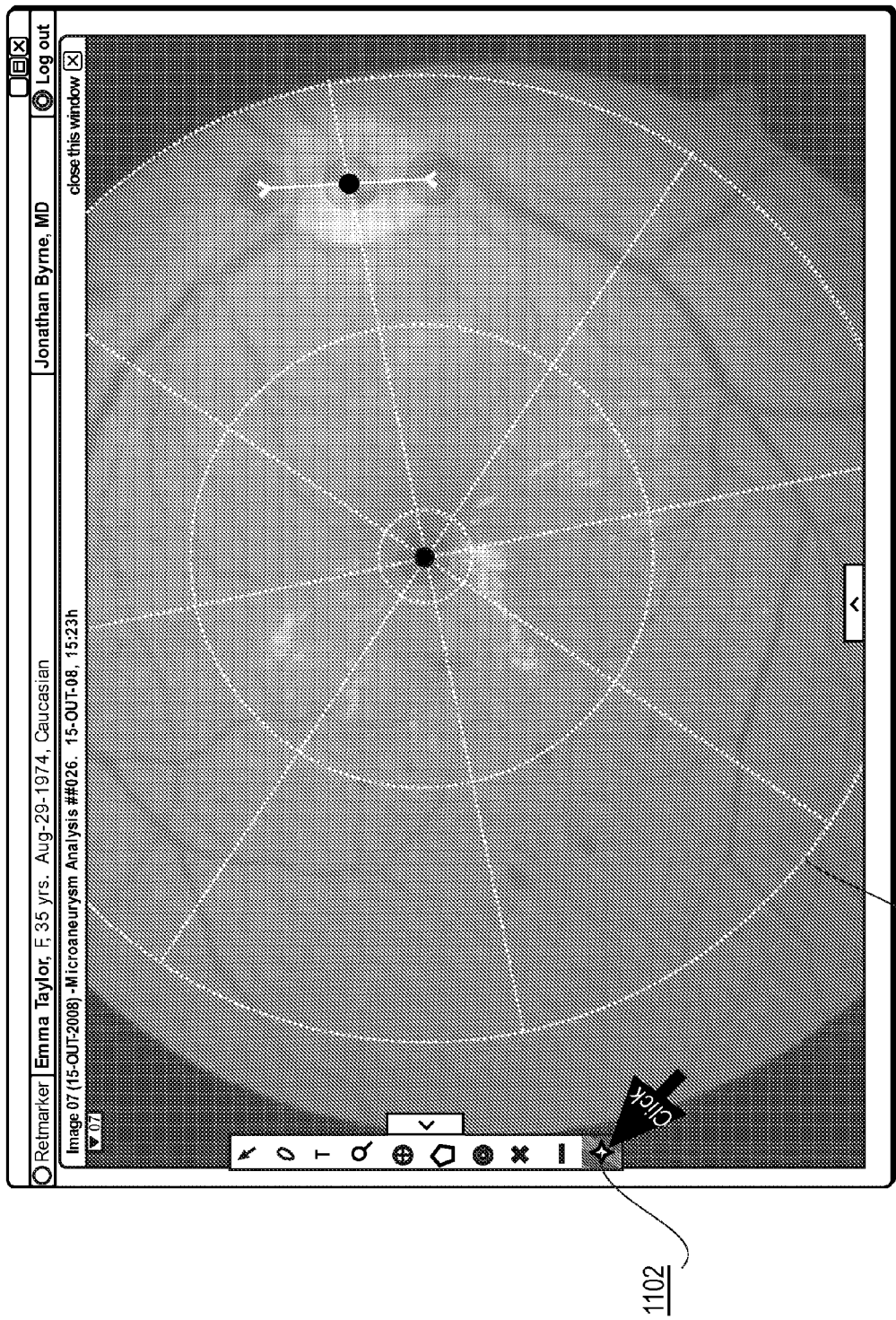
FIG. 11 illustrates an example of the use of a calibration tool for an instantiation of the present invention when executing on a computer system such as that illustrated in FIG. 1.

FIG. 11 illustrates an example of the use of the calibration tool. By selecting the icon 1102 representing the calibration tool, a set of axes 1104 are displayed, overlaying the image under consideration. The system automatically detects the optic disc and fovea center and positions the axes accordingly. This positioning needs to be confirmed by the user. The calibration tool is used in conjunction with the measurement tool. The system assumes the optic disc diameter to be 1500 µm in size and calibrates the measurement tool accordingly. Updates by the user are adjusted to the referenced measurements and these changes are saved.

Figure 12:
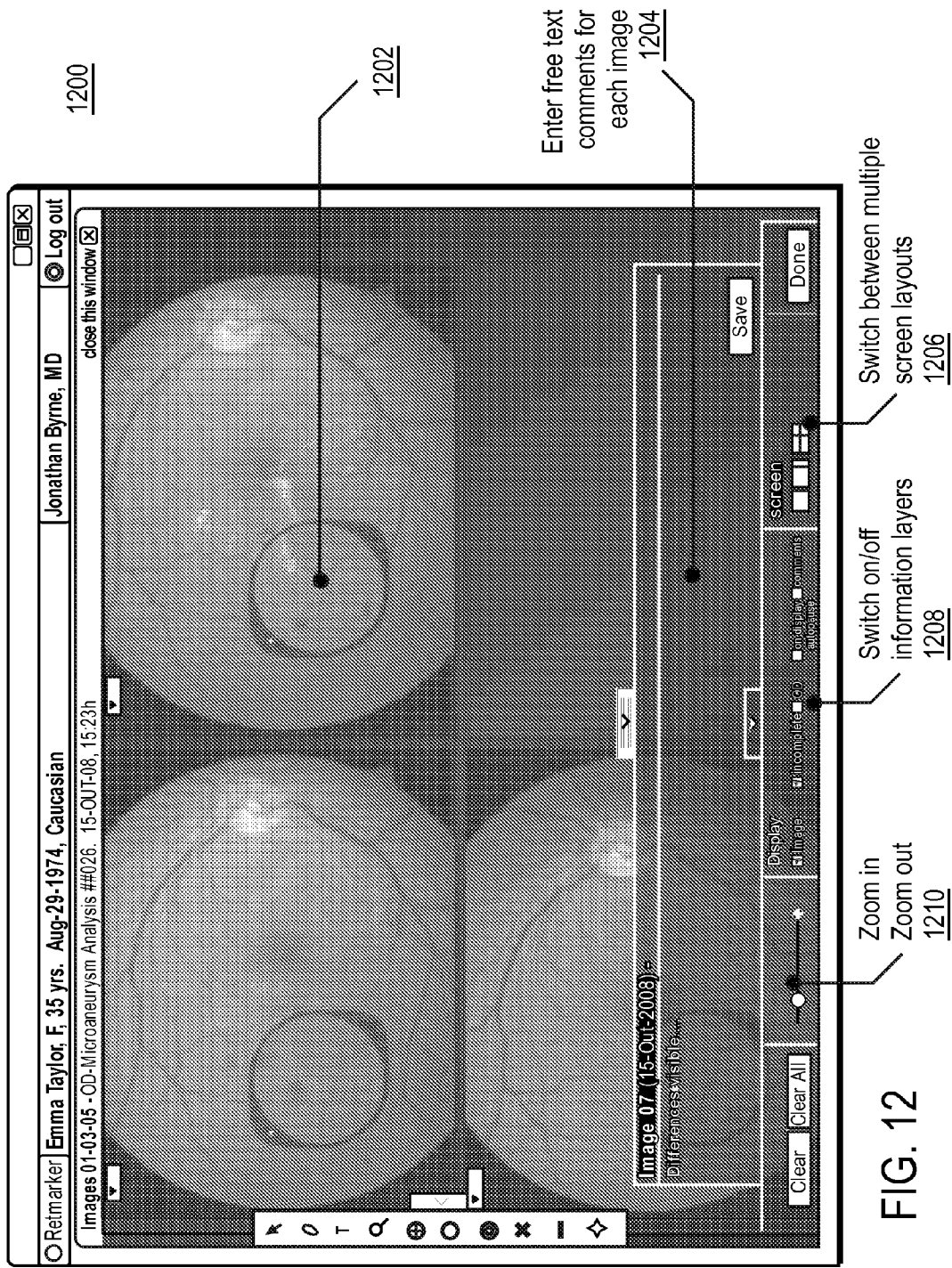
FIG. 12 illustrates an example of an image explorer screen for an instantiation of the present invention when executing on a computer system such as that illustrated in FIG. 1.

FIG. 12 illustrates an example of an image explorer screen 1200, this one being configured for co-registered, side-by-side display of multiple images. From this screen, any image can be selected for full screen view. Further, the magnifier lens tool 1202 is shown overlaying the images and provides a higher resolution, i.e., a zoom, user-configurable using a mouse wheel, view of the portion of the image over which it is positioned. This allows for detailed comparison of common areas of different images, e.g., that were captured at different times. From the image explorer, users can enter comments in a text field 1204, switch between various screen layouts 1206 (allowing for single or multiple images to be viewed), turn on or off various information layers 1208 (such as commenting field 1204), and zoom in or out 1210 to review the images being displayed.

Figure 13:
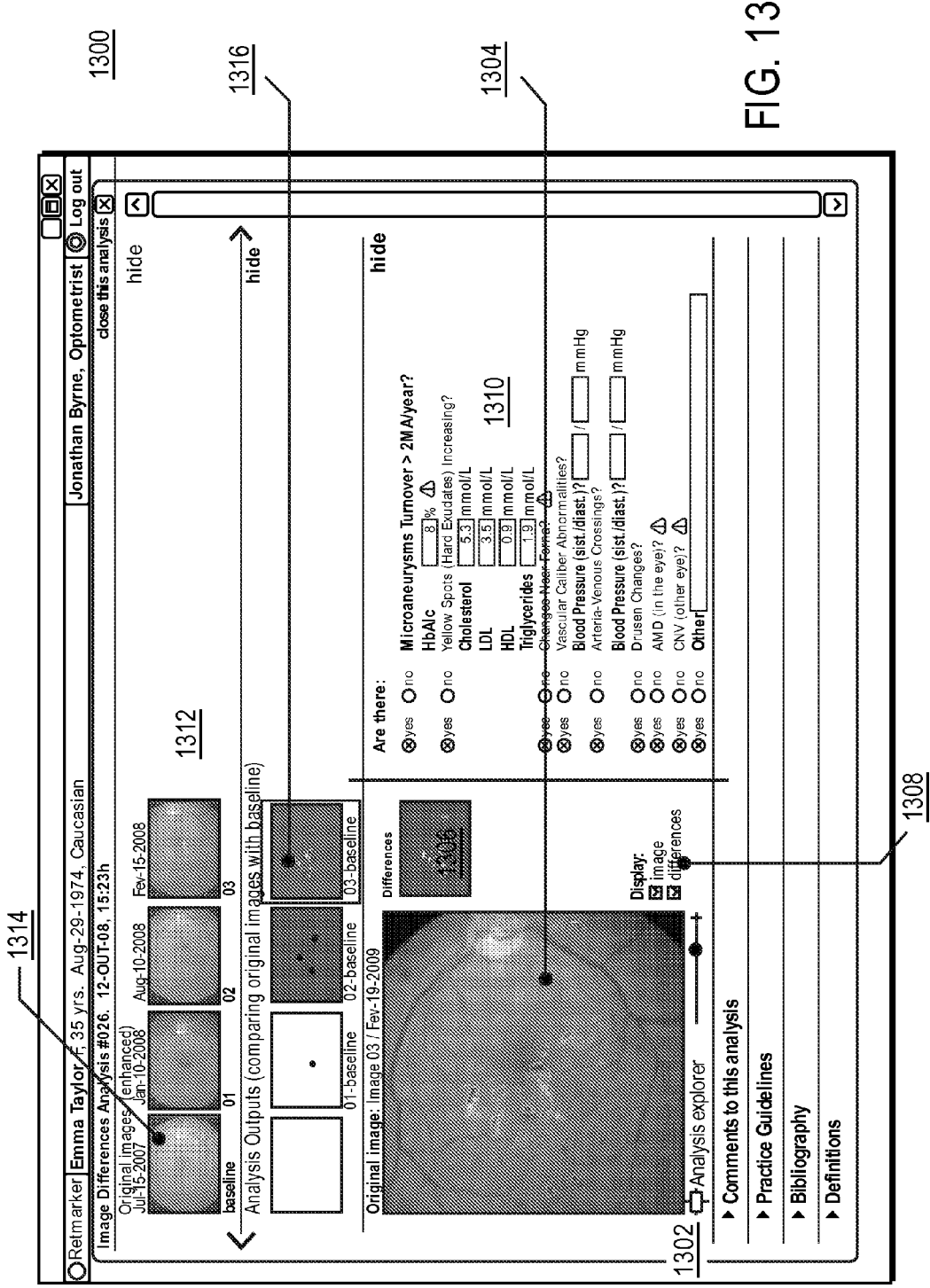
FIG. 13 illustrates an example of a differences analysis output screen for an instantiation of the present invention, in particular for the detection and identification of differences between a baseline image and images of an image set, when executing on a computer system such as that illustrated in FIG. 1.

Referring now to FIG. 13, an example of the differences analysis output screen 1300 is shown. Within the differences analysis output screen an analysis explorer 1302 is provided. The analysis explorer contains a toolset similar to that described above, to allow the user to document (e.g., using pencil and pointer tools), zoom in (using a magnifying lens tool), comment (using a text tool), measure (using a ruler tool)

and compare all features in each individual image included in an analysis. Special tools allow the user to designate or mark (e.g., with appropriate icons) features as hemorrhages, exudates, vascular caliber abnormalities, or drusens. A documentation area 1310 allows the user to review findings and annotate the analysis.

Along with a preview of an individual image 1304, the difference information 1306 (as determined from a comparison of the subject image with the baseline or reference image) is shown. A toggle control 1308 allows this information to be hidden or displayed, at the user's option. Individual images from the analyzed image set can be viewed as thumbnails in the image panel 1312, and the baseline image 1314 is also available. Below the images, thumbnails 1316 of the differences between the individual images and the baseline are presented.

Within the context of the present invention, a difference can be any change in morphology, color, brightness or contrast in the same region of an eye as between a reference image and a comparison image. Differences that are found during an analysis can be overlaid on top of the baseline image for easy reference.

Thus, systems and methods for analyzing digital color fundus images have been described. Of course, the forgoing discussion of certain illustrated embodiments of the invention were not intended to place limits thereon. A variety of other screens and functions can be provided through the present system. The invention should, therefore, only be measured in terms of the claims, which now follow.

What is claimed is:

1. A system, comprising:
a processor communicatively coupled to a storage device, said storage device storing computer-executable instructions, which instructions, when executed by the processor cause the processor to operate as:
a record module configured to permit importing of digital color fundus images for processing by said system;
an image set module configured to group two or more of said images for analysis, each group of images considered as an analysis set of images;
a processing module configured to generate analysis information for a selected analysis set of images by pre-processing constituent images of the selected analysis set of images to produce pre-processed images, co-registering the pre-processed images to produce co-registered images and analyzing the co-registered images to automatically identify pathological markers of retinopathy through automated detection of differences in the constituent images of the selected analysis set of images, to indicate either progression or regression of said pathological markers of retinopathy based on analysis of said analysis set of images, and to present clinically relevant information including numbers of microaneurysms that appeared and that suffered occlusion during a patient follow-up period; and
an analysis tool configured to provide a user a view of the analysis information and to collect inputs and instructions from a user via one or more tools of a graphical user interface.

2. A system according to claim 1, wherein said record module is configured to associate with each respective imported image, one or more of the following:
a date of the respective image;
an indication of whether the respective image is of a right or left eye;
information concerning equipment used to capture the respective image;
information concerning a field of acquisition for the respective image;
information concerning an angle of acquisition for the respective image;
information concerning whether or not mydriasis was used at the time of acquisition of the respective image.

3. A system according to claim 1, wherein said image set module is configured to group said images in response to user input in a chronological manner, or with respect to a selected reference image.

4. A system according to claim 1, wherein said image pre-processing comprises enhancing said images by changes in contrast and brightness.

5. A system according to claim 1, wherein automated identification of pathological markers of retinopathy further includes one or more of: detection, identification and quantification of microaneurysms; and detection and identification of other relevant pathological markers of retinopathy.

6. A system according to claim 5, wherein said detection and identification of microaneurysms comprises automatically detecting and identifying microaneurysms in identified ones of said constituent images of the selected analysis set of images.

7. A system according to claim 1, wherein said processing module is further configured to retrieve information through computation of positions and areas of detected pathological signs of retinopathy in analyzed ones of said analysis set of images, and suggestion of recommended actions according to a decision tree.

8. A system according to claim 7, wherein the computation of positions and areas of detected pathological signs of retinopathy in analyzed ones of said analysis set of images comprises computation of positions of microaneurysms and surface areas of other detected pathological signs of retinopathy in the analyzed ones of said analysis set of images.

9. A system according to claim 7, wherein said suggestion of recommended actions comprises guidelines for therapeutic action.

10. A system according to claim 1, wherein the clinically relevant information further includes some or all of: microaneurysm formation rate; microaneurysm disappearance rate; and microaneurysms activity level by means of numbers of microaneurysms at each patient visit.

11. A system according to claim 1, wherein the analysis tool is configured to receive as inputs said images and to return information regarding said images according to computations performed by said processing module.

12. A system according to claim 1, wherein the analysis tool includes a log-in module, a main page module, a patient module, a patient dashboard, and an image explorer.

13. A system according to claim 12, wherein said log-in module is configured to accept user identification credentials including a user name and password.

14. A system according to claim 12, wherein the main page module includes a user dashboard, a patient list, a search page, and a new patient module.

15. A system according to claim 14, wherein said user dashboard includes a list of submitted analysis jobs and status of the submitted analysis jobs.

16. A system according to claim 12, wherein said patient dashboard comprises those of said images related to a patient identified by said dashboard, and analysis results relevant for said patient identified by said dashboard.

17. A system according to claim 12 wherein said patient dashboard includes means to submit new analyses for a patient identified by said dashboard.

* * * * *